(12) United States Patent
Torchia et al.

(10) Patent No.: US 6,418,337 B1
(45) Date of Patent: Jul. 9, 2002

(54) MRI GUIDED HYPERTHERMIA SURGERY

(75) Inventors: Mark G. Torchia; Richard Tyc; Ken J. McTaggart; John S. Pacak, all of Winnipeg (CA)

(73) Assignee: Autolitt Inc., Winnipeg (CA)

( * ) Notice: Subject to any disclaimer, the term of this patent is extended or adjusted under 35 U.S.C. 154(b) by 12 days.

(21) Appl. No.: 09/593,699

(22) Filed: Jun. 15, 2000

(51) Int. Cl.⁷ .................................................. A61B 5/05
(52) U.S. Cl. ...................... 600/411; 600/412; 600/417; 604/20; 606/13; 606/14; 606/15; 606/17; 606/27
(58) Field of Search .................................. 364/557, 315, 364/304, 413.13; 607/159, 88, 89; 606/130, 1, 2, 13–17, 27; 600/407, 410, 411, 412, 417; 601/5; 604/20

(56) References Cited

U.S. PATENT DOCUMENTS

| | | | |
|---|---|---|---|
| 4,671,254 A | | 6/1987 | Fair |
| 4,914,608 A | | 4/1990 | LeBihan et al. |
| 5,284,144 A | * | 2/1994 | Delannoy et al. ........... 324/315 |
| 5,291,890 A | | 3/1994 | Cline et al. |
| 5,327,884 A | * | 7/1994 | Hardy et al. ............. 128/653.2 |
| 5,368,031 A | * | 11/1994 | Cline et al. .............. 128/653.2 |
| 5,492,122 A | * | 2/1996 | Button et al. ............. 128/653.2 |
| 5,733,277 A | | 3/1998 | Pallarito |
| 5,823,941 A | | 10/1998 | Shaunnessey |
| 6,128,522 A | | 10/2000 | Acker et al. |
| 6,246,896 B1 | * | 6/2001 | Dumoulin et al. .......... 600/411 |
| 6,280,384 B1 | * | 8/2001 | Loeffler ...................... 600/412 |
| 6,293,282 B1 | * | 9/2001 | Lemelson .................. 128/899 |
| 6,332,891 B1 | * | 12/2001 | Himes ........................ 606/130 |

FOREIGN PATENT DOCUMENTS

| | | |
|---|---|---|
| EP | 0 614 651 A1 | 9/1994 |
| WO | WO 98/52465 | 11/1998 |

* cited by examiner

*Primary Examiner*—Marvin M. Lateef
*Assistant Examiner*—Jeoyuh Lin
(74) *Attorney, Agent, or Firm*—Adrian D. Battison; Michael R. Williams (57) ABSTRACT

An MRI guided surgical apparatus includes a heat source formed by a laser and an optical fiber carrying the heat energy into a part to be coagulated by hyperthermia with an end reflector to direct the energy in a beam to one side of the fiber end. The fiber includes a reinforcing sleeve along its length to prevent bending and twisting. The sleeve is mounted in a shielded, Piezo-electric motor which causes movement of the fiber longitudinally of its axis to move the end within the part and rotation of the fiber about its axis to cause the beam to rotate about the axis. A rigid elongate cannula is arranged for insertion to a position at the part of the patient having a bore for receiving a portion of the fiber adjacent the outlet end in sliding engagement therein such that the end can pass through the cannula into engagement with the part of the patient. A part of the sleeve projecting beyond the cannula is rigid and a further part connecting to the motor is stiff but less rigid. A magnetic resonance imaging system is arranged to generate a series of output signals over a period of time representative of temperature in the part as the temperature of the part changes during that time. The heat source is controlled in heat energy applied and location and orientation of the beam to continue the heating at a respective area in the part until the temperature at a selected location in the part normally at the boundary of a tumor reaches the required hyperthermic temperature as monitored whereupon the heating in the area is halted.

36 Claims, 7 Drawing Sheets

MRI GUIDED HYPERTHERMIA SURGERY

This invention relates to an apparatus for hyperthermia surgery in a patient using a magnetic resonance imaging system to effect guiding and control of the heating source.

BACKGROUND OF THE INVENTION

The excision of tumours by hyperthermia is known. Thus tumours and other masses to be excised can be heated above a predetermined temperature of the order of 55° C. so as to coagulate the portion of tissue heated. The temperature range is preferably of the order of 55 to 65° C. and does not reach temperatures which can cause ablation of the tissue.

One technique for effecting the heating is to insert into the mass concerned an optical fiber which has at its inserted end an element which redirects laser light from an exterior source in a direction generally at right angles to the length of the fiber. The energy from the laser thus extends into the tissue surrounding the end or tip and effects heating. The energy is directed in a beam confined to a relatively shallow angle so that, as the fiber is rotated, the beam also rotates around the axis of the fiber to effect heating of different parts of the mass at positions around the fiber. The fiber can thus be moved longitudinally and rotated to effect heating of the mass over the full volume of the mass with the intention of heating the mass to the required temperature without significantly affecting tissue surrounding the mass.

At this time the fiber is controlled and manipulated by a surgeon with little or no guidance apart from the knowledge of the surgeon of the anatomy of the patient and the location of the mass. It is difficult therefore for the surgeon to effect a controlled heating which heats all of the tumour while minimizing damage to surrounding tissue.

It is of course well known that the location of tumours and other masses to be excised can be determined by imaging using a magnetic resonance imaging system. The imaging system thus generates for the surgeon a location of the mass to be excised but there is no system available which allows the surgeon to use the imaging system to control the heating effect. In most cases it is necessary to remove the patient from the imaging system before the surgery commences and that movement together with the partial excision or coagulation of some of the tissue can significantly change the location of the mass to be excised thus eliminating any possibility for controlled accuracy.

It is also known that magnetic resonance imaging systems can be used by modification of the imaging sequences to determine the temperature of tissue within the image and to determine changes in that temperature over time.

U.S. Pat. No. 4,914,608 (LeBiahan) assigned to U.S. Department of Health and Human Services issued Apr. 3, 1990 discloses a method for determining temperature in tissue.

U.S. Pat. No. 5,284,144 (Delannoy) also assigned to U.S. Department of Health and Human Services and issued Feb. 8, 1994 discloses an apparatus for hyperthermia treatment of cancer in which an external non-invasive heating system is mounted within the coil of a magnetic resonance imaging system. The disclosure is speculative and relates to initial experimentation concerning the viability of MRI measurement of temperature in conjunction with an external heating system. The disclosure of the patent has not led to a commercially viable hyperthermic surgery system.

U.S. Pat. Nos. 5,368,031 and 5,291,890 assigned to General Electric relate to an MRI controlled heating system in which a point source of heat generates a predetermined heat distribution which is then monitored to ensure that the actual heat distribution follows the predicted heat distribution to obtain an overall heating of the area to be heated. Again this patented arrangement has not led to a commercially viable hyperthermia surgical system.

An earlier U.S. Pat. No. 4,671,254 (Fair) assigned to Memorial Hospital for Cancer and Allied Diseases and issued Jun. 9, 1987 discloses a method for a non surgical treatment of tumours in which the tumour is subjected to shock waves. This does not use a monitoring system to monitor and control the effect.

SUMMARY OF THE INVENTION

It is one object of the present invention, therefore, to provide an improved method and apparatus for effecting controlled surgery by hyperthermia.

According to a first aspect of the invention there is provided a method for effecting surgery by hyperthermia comprising:

providing a heat source arranged to apply heat to a part of a patient on whom the surgery is to be effected;

operating a non-invasive detection system to generate a series of output signals over a period of time representative of temperature in the part as the temperature of the part changes during that time;

identifying a plurality of locations in the part to be heated to a required hyperthermic temperature;

using the output signals to monitor the temperature at the locations as the temperature changes over the period of time;

for each location, controlling the heat source to effect heating of an area of the part adjacent the location;

and, for each location, continuing the heating at the respective area until the temperature at the location reaches the required hyperthermic temperature as monitored whereupon the heating in the area is halted.

Preferably the heat source is controlled by controlling an amount of heat generated thereby and by controlling a selected area of the part to which the heat is applied.

Preferably the monitored locations are arranged at an outer periphery of a volume to be heated to the required hyperthermic temperature.

Preferably the method includes identifying the locations at the outer periphery of the volume, generally a tumor, to be heated from a preliminary series of signals from the non-invasive detection system.

Preferably the heat source is provided on an invasive probe inserted into the part and wherein the control of the heat source is effected by moving the probe. However other non-invasive but directional heating techniques can be used such as ultra-sound and other radiations.

Preferably the heat source is provided on an invasive probe and is arranged to cause heating in a predetermined direction relative to the probe and wherein the control of the heat source is effected by moving the probe to alter the direction.

Preferably the heat source comprises a laser, an optical fiber for communicating light from the laser, a mounting for the optical fiber allowing invasive insertion of an end of the fiber into the part of the patient, a light directing element at an end of the fiber for directing the light from the laser to a predetermined direction relative to the fiber and a position control system for moving the end of the fiber.

Preferably there is provided a cannula through which the fiber is inserted, the cannula having an end which is moved to a position immediately adjacent but outside the part to be heated and the fiber having a rigid end portion projecting from the end of the cannula into the part.

According to a second aspect of the invention there is provided an apparatus for effecting surgery by hyperthermia comprising:

a heat source arranged to apply heat to a part of a patient on whom the surgery is to be effected;

a non-invasive detection system arranged to generate a series of output signals over a period of time representative of temperature in the part as the temperature of the part changes during that time;

and a control system comprising:

a first means arranged to identify a plurality of locations in the part to be heated to a required hyperthermic temperature;

a second means arranged to use the output signals to monitor the temperature at the locations as the temperature changes over the period of time;

and a third means arranged to control the heat source to effect heating of an area of the part adjacent each location;

the control system being arranged in response to said temperatures at the locations to operate the third means to control the selection of the area to which heat is applied and to control the amount of heat applied to the area.

Preferably the control system includes a first control for controlling an amount of heat generated by the heat source and a second control for moving the heat source to effect heating at a selected area of the part to which the heat is applied.

Preferably the heat source comprises: an optical fiber having an inlet end and an outlet end; a laser source for supplying light energy into the fiber at the inlet end; a light deflector at the outlet end for directing the light in a beam at an angle to a longitudinal axis of the fiber at the outlet end such that rotation of the fiber about the axis causes the beam to rotate about the axis; and a rigid elongate cannula arranged for insertion to a position at the part of the patient; the cannula having a bore arranged for receiving a portion of the fiber adjacent the outlet end in sliding engagement therein such that the end can pass through the cannula into engagement with the part of the patient.

Preferably the third means of the control system comprises a drive assembly for causing a first longitudinal movement of the fiber relative to the cannula along its length and for causing a second rotational movement of the fiber about its axis.

Preferably there is provided a mounting for the drive assembly for supporting the drive assembly exteriorly of the cannula and wherein the fiber has a reinforcing sleeve member surrounding and attached to a portion of the fiber so as to extend from the drive assembly to the outlet end, the sleeve member holding the fiber against lateral bending during said longitudinal movement and against torsional twisting during said rotational movement and the sleeve member being arranged to extend through the cannula.

Preferably the sleeve includes at least a portion which is integrally molded from a fiber reinforced polymer.

Preferably the sleeve includes a first portion at the outlet end which is formed of a first material, such as glass which is substantially rigid to rigidly support that portion of the fiber projecting in cantilever manner beyond the end of the cannula and a second portion connected to and extending from the first portion to the drive assembly, the second portion being formed of a second material such as liquid crystal polymer which is stiff but less rigid than the first portion to allow some flexing when the fiber is inserted into the cannula. In another arrangement, the sleeve can be wholly formed from a material which allows the necessary stiffness but does not have the brittleness of for example glass.

Preferably the reinforcing sleeve includes an engagement portion attached thereto for engaging the drive assembly including a portion of polygonal cross-section for engaging into a drive collar of corresponding cross-section of the drive assembly for driving rotational movement of the fiber and including a shoulder section for engaging against a drive member of the drive assembly for driving longitudinal movement of the fiber.

Preferably the non-invasive detection system comprises a magnetic resonance imaging system including a magnet to generate a magnetic field for the imaging system and an antenna for detecting radio frequency signals from the part of the patient; and wherein the third means of the control system includes a member located within and arranged to be moved within the magnetic field and a motor for driving movement of the member, the motor including no ferro-magnetic components such that it is usable in the magnetic field and the motor and a drive coupling thereto being shielded by a surrounding conductor to prevent interference with the radio frequency signals.

Preferably the third means of the control system includes a driven member rotatable about an axis and a reciprocating drive element arranged to cause a ratcheting movement of the driven member.

Preferably the reciprocating drive element comprises a piezo-electric motor.

Preferably one driven member includes a sleeve arranged to receive the fiber therethrough and the fiber and sleeve are non circular or polygonal in shape such that rotation of the member causes rotation of the fiber about the axis while allowing longitudinal sliding movement of the fiber relative to the sleeve.

Preferably one driven member has a female threaded bore therein and wherein the fiber has attached thereto a screw engaging the bore such that rotation of the driven member about the axis causes the screw to effect movement of the fiber longitudinally along the axis.

According to a third aspect of the invention there is provided an apparatus comprising:

a magnetic resonance imaging system arranged to generate an image from a sample and including a magnet to generate a magnetic field and an antenna for detecting radio frequency signals from the sample;

a member located within and arranged to be moved within the magnetic field;

and a motor having a drive coupling thereto for driving movement of the member, the motor including a reciprocating element for generating a motive force for the motor;

the motor including no ferro-magnetic components such that it is usable in the magnetic field and the motor and the drive coupling being shielded by a surrounding conductor to prevent interference with the radio frequency signals.

According to a fourth aspect of the invention there is provided an apparatus for laser surgery on a part of a patient comprising:

an optical fiber having an inlet end and an outlet end;

a laser source for supplying light energy into the fiber at the inlet end;

a light deflector at the outlet end for directing the light in a beam at an angle to a longitudinal axis of the fiber at the outlet end such that rotation of the fiber about the axis causes the beam to rotate about the axis;

a rigid elongate cannula arranged for insertion into the part of the patient;

the cannula having a bore arranged for receiving a portion of the fiber adjacent the outlet end in sliding engagement therein such that the end can pass through the cannula into engagement with the part of the patient;

a drive assembly for causing a first longitudinal movement of the fiber relative to the cannula along its length and for causing a second rotational movement of the fiber about its axis;

the fiber having a reinforcing sleeve member surrounding and attached to a portion of the fiber adjacent the outlet end, the sleeve member holding the fiber against lateral bending during said longitudinal movement and against torsional twisting during said rotational movement.

According to a fifth aspect of the invention there is provided a method for effecting surgery comprising:

providing a radiation source arranged to apply radiation to a part of a patient on whom the surgery is to be effected, the radiation being arranged to cause ablation of the part;

operating a non-invasive detection system to generate a series of output signals over a period of time representative of the effect of the radiation in the part as the radiation affects the part during that time;

identifying a plurality of locations in the part to ablated;

using the output signals to monitor the effect of the radiation at the locations as the radiation affects the part over the period of time;

for each location, controlling the radiation source to effect ablation of an area of the part adjacent the location;

and, for each location, continuing the radiation at the respective area until the effect of the radiation at the location reaches the required ablation as monitored whereupon the radiation in the area is halted.

It will be noted therefore that the ablation of the part can be effected by other forms of controlled directional radiation other than heat. The radiation is directed to the tip of the probe and controlled in direction and location while the effect of the radiation is monitored. Various forms of radiation can be used provided they are directional and controllable and effect ablation of the part.

Preferably the monitored locations define an outer periphery of a volume such as a tumour to be ablated.

Preferably the method includes identifying the outer periphery of the volume to be ablated from a preliminary series of signals from the non-invasive detection system and monitoring the effect of the radiation over the full area defined by the outer periphery.

Preferably the radiation source is provided on an invasive probe inserted into the part and wherein the control of the radiation source is effected by moving the probe.

BRIEF DESCRIPTION OF THE DRAWINGS

One embodiment of the invention will now be described in conjunction with the accompanying drawings in which.

DETAILED DESCRIPTION

Figure 1:
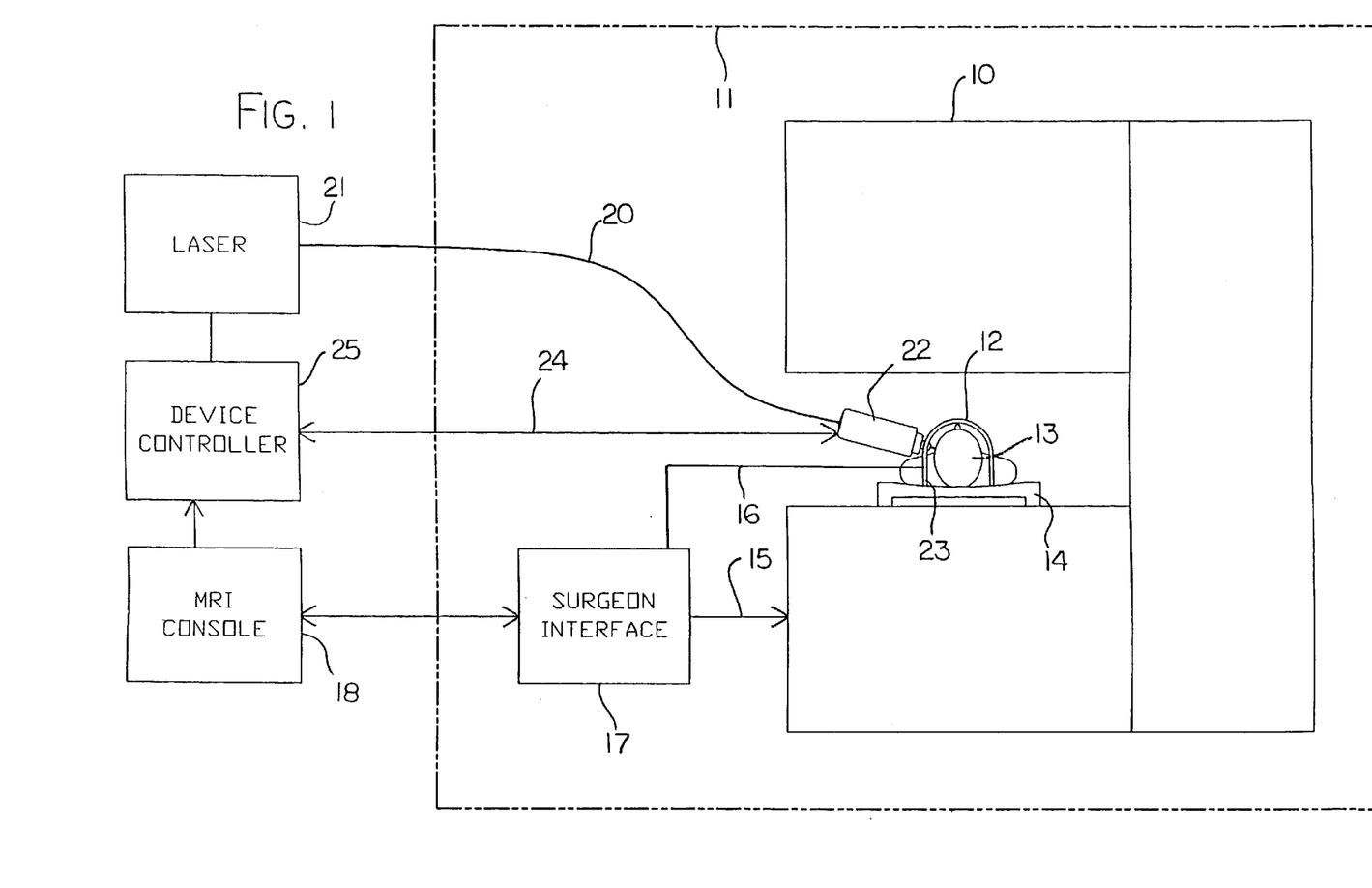
FIG. 1 is a schematic illustration of an apparatus for effecting MRI guided laser surgery according to the present invention.

In FIG. 1 is shown schematically an apparatus for carrying out MRI controlled laser surgery. The apparatus comprises a magnetic resonance imaging system including a magnet 10 provided within a shielded room 11. The magnet 10 can be of any suitable construction and many different magnet arrangements are available from different manufacturers. The magnet includes field coils for generating variations in the magnetic field which are not shown since these are well known to one skilled in the art together with a radio frequency antenna coil which receives signals from the sample in this case indicated as a human patient 13.

The patient 13 rests upon a patient support table 14 on which the patient is supported and constrained against movement for the operative procedure. The fields of the magnet are controlled on an input control line 15 and the output from the antenna coil is provided on an output line 16 both of which communicate through a surgeon interface 17 to the conventional MRI control console 18. The MRI console and the magnet are shown only schematically since these are well known to one skilled in the art and available from a number of different manufacturers.

The apparatus further includes a laser surgery system including an optical fiber 20 which transmits heat energy in the form of light from a laser 21 mounted outside the room 11. The fiber extends into the room to a tip 21 (FIG. 2) at which the energy escapes into the relevant part of the patient as discussed hereinafter. The position of the fiber 20 within the patient and the orientation of the fiber is controlled by a drive motor 22 supported in fixed adjustable position on a stereotaxic frame 23. The motor communicates through a control line 24 to a device controller 25. In general the device controller receives information from the MRI console and from position detectors of the motor 22 so as to operate movement of the motor 22 and to operate a power output from the laser 21 so as to control the position and amount of heat energy applied to the part within the body of the patient.

Figure 2:
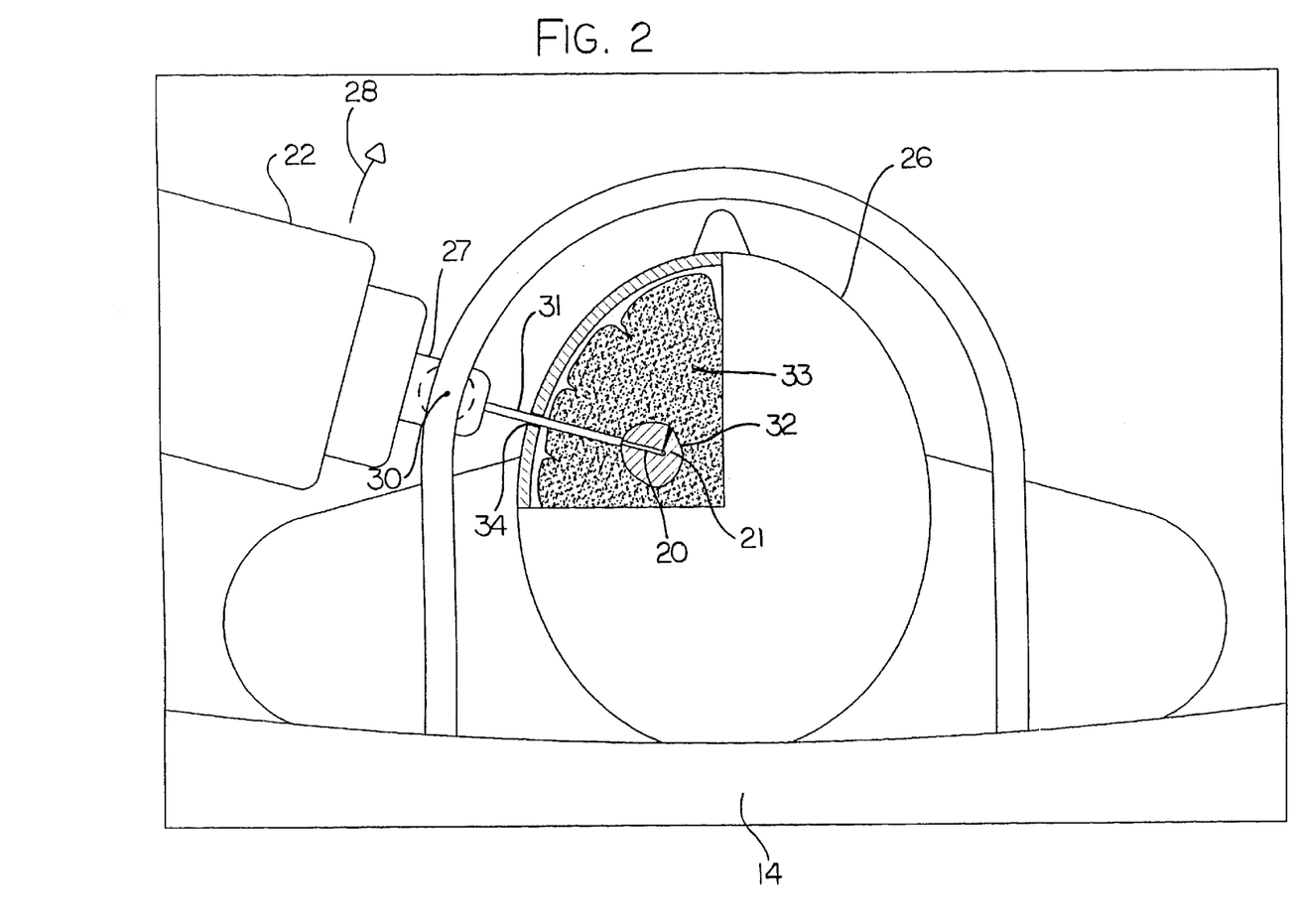
FIG. 2 is a schematic illustration of the apparatus of FIG. 1 on an enlarged scale and showing the emission of laser energy into the brain of a patient.

In FIG. 2 is shown on a larger scale the patient table 14 to which is attached the stereotaxic frame 23 so that the frame is fixed relative to the table and extends over the head 26 of the patient. The frame is shown schematically and suitable details will be well known to one skilled in the art, but carries the motor 22 in a position on the frame by a bracket 27 of the motor. The position of the motor on the frame remains fixed during the procedure but can be adjusted in the arcuate direction 28 around the arch of the frame 23. The frame 23 can also be adjusted forwardly and rearwardly on the table 14. The bracket 27 also allows rotation of the motor about a point 30 within the frame so that the direction of the fiber projecting forwardly from the motor can be changed relative to the frame.

The apparatus further includes a rigid cannula 31 which surrounds the fiber 20 and which is arranged to allow sliding movement of the fiber longitudinally in the cannula and rotational movement within the cannula while generally holding the fiber in a direction axial of the cannula. The cannula is formed of a suitable rigid ceramic material so that it is stiff and resistant to bending and has sufficient strength to allow the surgeon to insert the cannula into the required location within the body part of the patient.

In the arrangement as shown, the apparatus is arranged for operating upon a tumour 32 within the brain 33 of the patient. The surgeon therefore creates an opening 34 in the skull of the patient and directs the cannula 31, in the absence of the fiber 20, through the opening 34 to the front edge of the tumour 32.

The position of the tumour is determined in an initial set of MRI experiments using conventional surgical and an analytical techniques to define the boundaries, that is a closed surface within the volume of the brain which constitutes the extremities of the tumour. The surgical analysis by which the surgeon determines exactly which portions of the material of the patient should be removed is not a part of this invention except to say that conventional surgical techniques are available to one skilled in the art to enable an analysis to be carried out to define the closed surface.

The angle of insertion of the cannula is arranged so that, of course, it avoids as far as possible areas of the patient which should not be penetrated such as major blood vessels and also so that the cannula is directed so that, when it reaches the outside surface, it points toward a center of the tumour.

Figure 3:
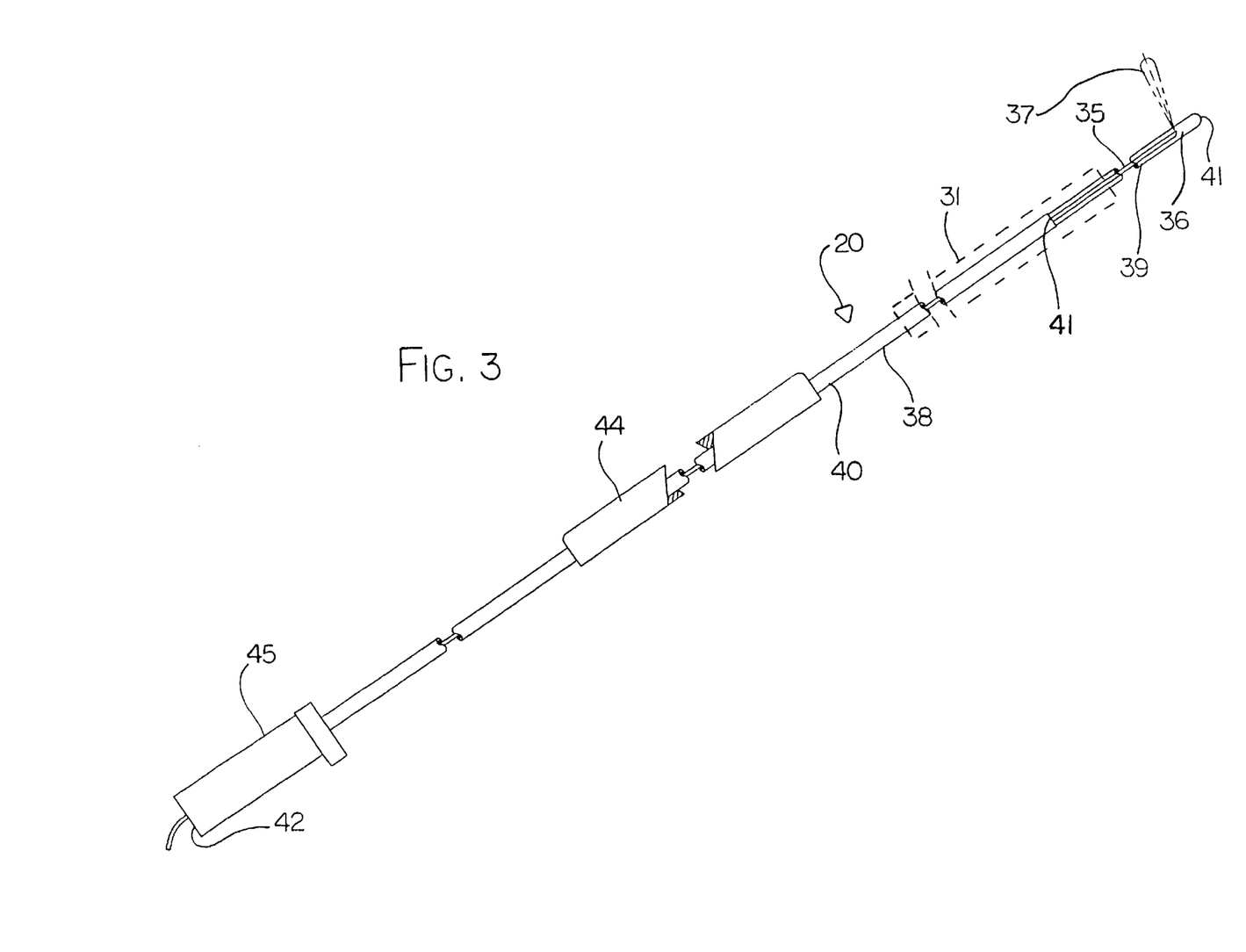
FIG. 3 is a side elevational view of the laser probe of the apparatus of FIG. 1.

The optical fiber structure generally indicated at 20 in FIG. 3 includes an actual glass fiber element 35 which has an inlet end (not shown) at the laser and a remote end 36. At the remote end is provided a reflector or prism which directs the laser energy in a beam 37 to one side of the end 36. Thus the beam 37 is directed substantially at right angles to the length of the fiber and over a small angle around the axis of the fiber. The beam 37 forms a cone having a cone angle of the order of 12 to 15 degrees. Such fibers are commercially available including the reflector or prism for directing the light at right angles to the length of the fiber.

The fiber element itself as indicated at 35 is however encased in an enclosure to allow the fiber to be manipulated in the motor 22. Around the fiber is formed a sleeve 38 including a first end portion 39 and a second longer portion 40. The end portion 39 encloses the end 36 which is spaced from a tip 41 of the end portion. The end portion extends over the length of the order of 7 to 11 cms. The longer second portion 38 is of the order of 48 to 77 cms in length and extends from a forward end 41 through to a rear end 42. The front portion 39 is formed of a rigid material such as glass. The longer rear portion 40 is formed of a stiff material which is less brittle than glass and yet maintains bending and tortional stiffness of the fiber so that forces can be applied to the sleeve portion 40 to move the tip 36 of the fiber to a required position within the tumour. The second portion 40 is formed of a material such as fiber reinforced plastics.

The two portions are bonded together to form an integral structure of common or constant diameter selected as a sliding fit through the cannula. The rigid front portion has a length so that it can extend from the end of the cannula at the forward or closest edge of the tumour through to the rear edge of the tumour. An average tumour might have a diameter of the order of 0.5 to 5.0 cms so that the above length of the forward portion is sufficient to extend through the full diameter of the tumour while leaving a portion of the order of 1.25 cms within the end of the cannula. In this way the substantially rigid forward portion maintains the forward portion of the fiber lying substantially directly along the axis of the cannula without any bending or twisting of the forward portion within the cannula. The longer second portion is not formed from glass since this would provide a complete structure which is too brittle to allow the surgeon to insert the structure into the cannula without the danger of cracking or fracturing the structure under any bending loads. A less brittle material is therefore selected which can accommodate some bending loads caused by manual insertion of the structure into the cannula and yet can communicate the forces from longitudinal and rotational movement as described herein after.

The sleeve portion 40 has attached to it a first polygonal or non-circular section 44 and a second end stop section 45. Both of the drive sections 44 and 45 are connected to the second portion so as to communicate driving action to the second portion. Thus the polygonal section 44 is arranged to co-operate with a drive member which acts to rotate the second portion and therefore the fiber along its full length about an axis longitudinal of the fiber. The second end stop section 45 is arranged to co-operate with a longitudinally movable drive element which moves the second portion and therefore the fiber longitudinally. In this way the tip 36 can be moved from an initial position in which it projects just beyond the outer end of the cannula outwardly into the body of the tumour until the tip reaches the far end of the tumour. In addition the tip can be rotated around the axis of the fiber so that the heat energy can be applied at selected angles around the axis. By selectively controlling the longitudinal movement and rotation of the tip, therefore, the heat energy can be applied throughout a cylindrical volume extending from the end of the cannula along the axis of the cannula away from the end of the cannula. In addition by controlling the amount of heat energy applied at any longitudinal position and angular orientation, the heat energy can be caused to extend to required depths away from the axis of the cannula so as to effect heating of the body part of the patient over a selected volume with the intention of matching the volume of the tumour out to the predetermined closed surface area defining the boundary of the tumour.

Figure 4:
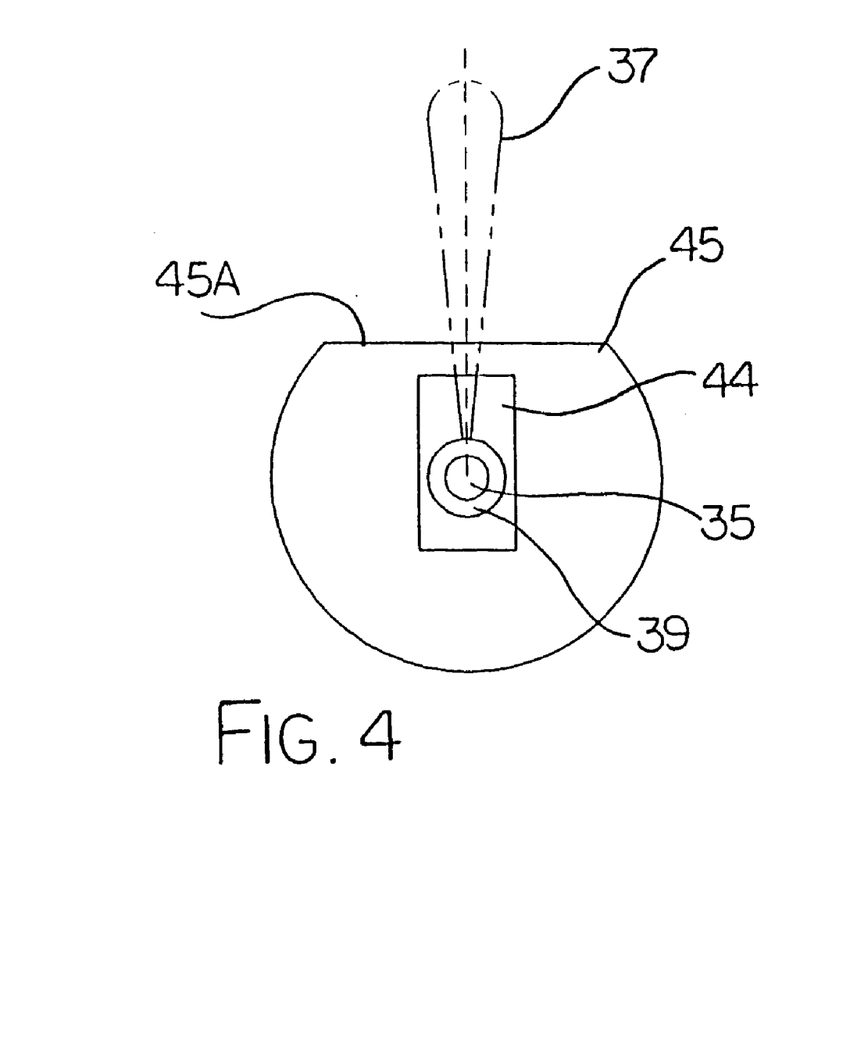
FIG. 4 is an end elevational view of the laser probe of the apparatus of FIG. 1.

As shown in FIG. 4, the non-circular cross section of the drive portion 44 is rectangular with a height greater than the width. However of course other non-circular shapes can be used provided that the cross section is constant along the length of the drive portion and provided that the drive portion can co-operate with a surrounding drive member to receive rotational driving force therefrom. The end stop member 45 is generally cylindrical with a top segment 45A removed to assist the operator in insertion of the fiber into the drive motor.

Figure 5:
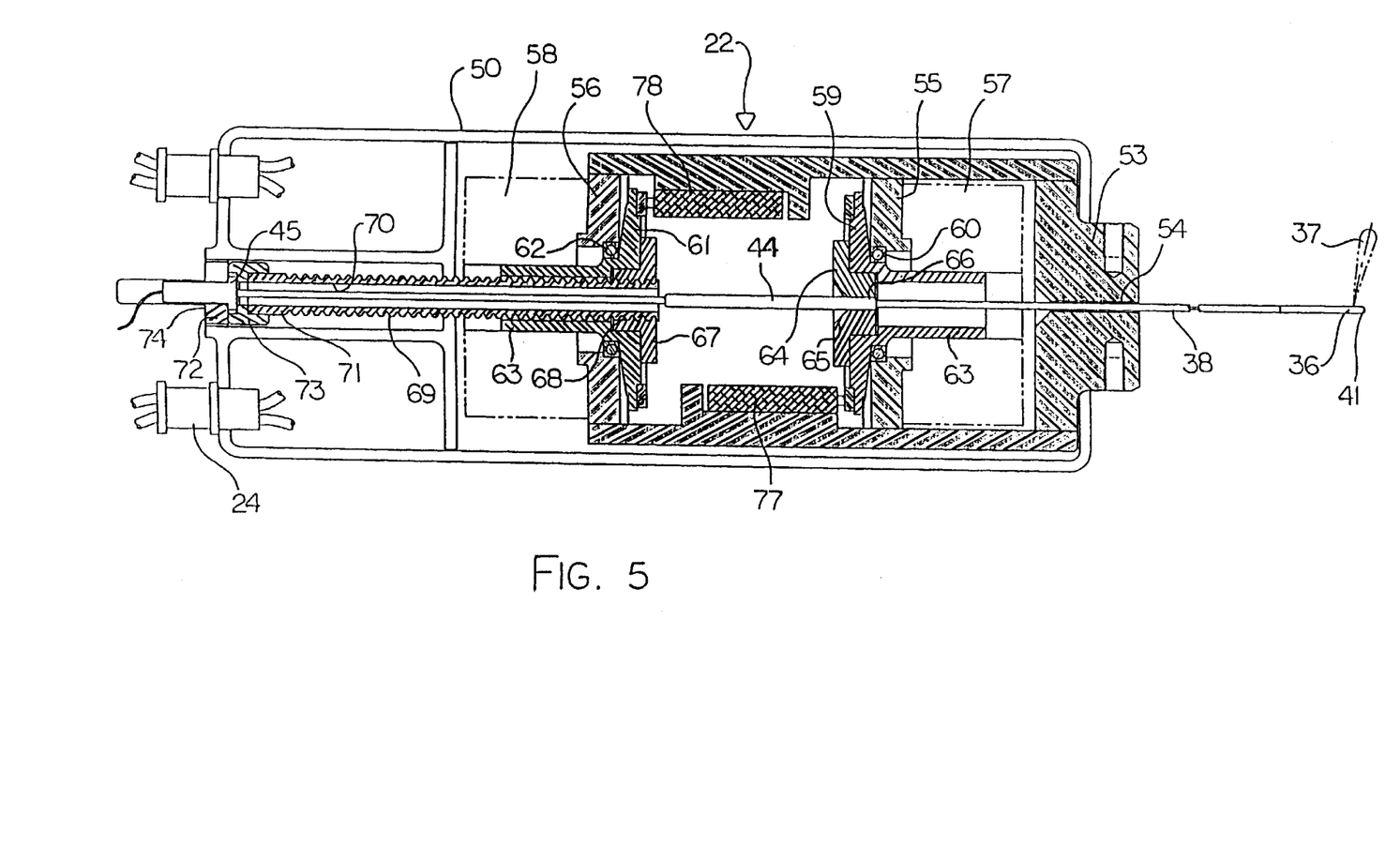
FIG. 5 is a cross sectional view of the laser probe and drive motor therefor of the apparatus of FIG. 1.
Figure 6:
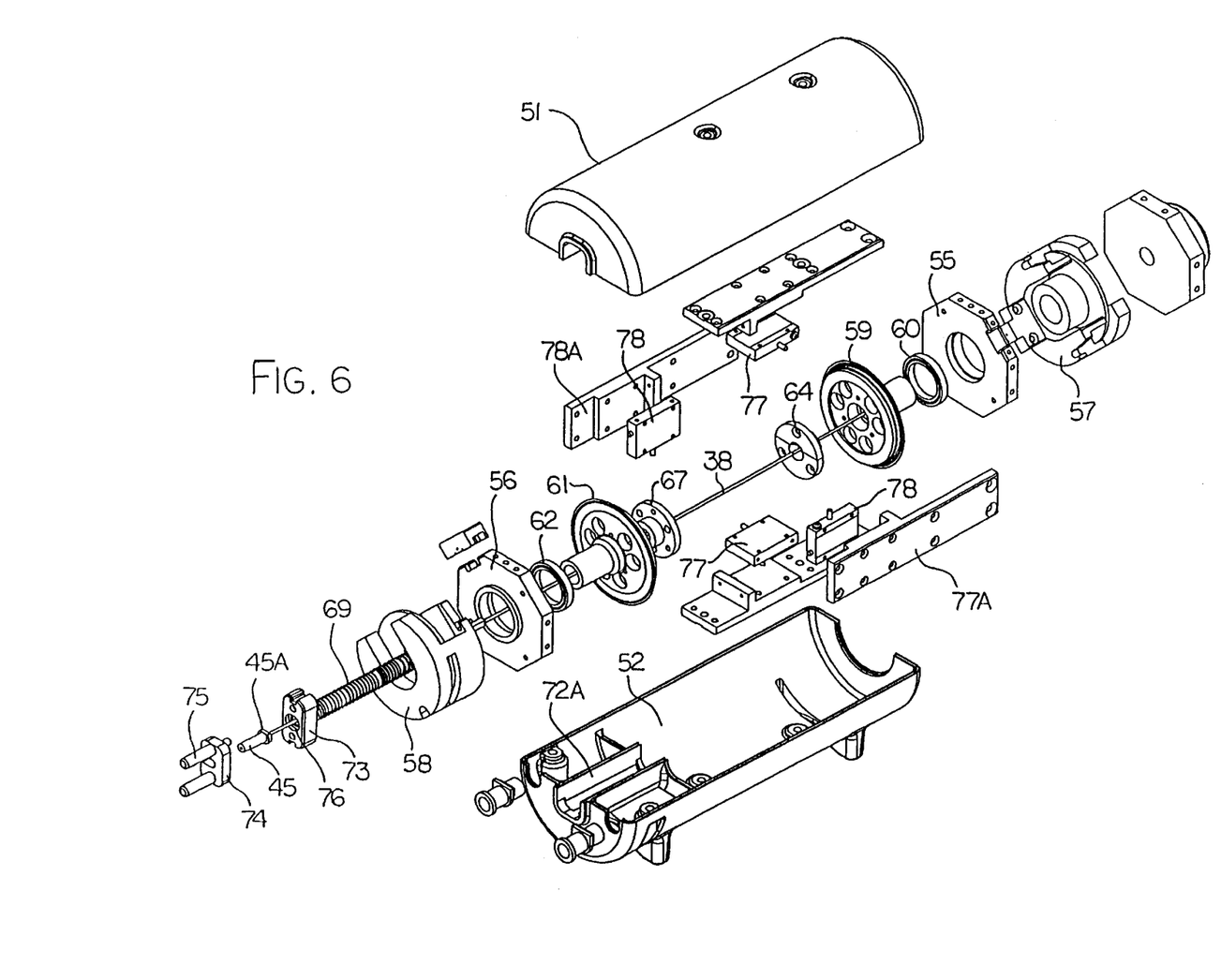
FIG. 6 is an exploded view of the drive motor of the apparatus of FIG. 1.

Turning now to FIGS. 5 and 6, the drive motor 22 is shown in more detail for effecting a driving action on the fiber through the drive members 44 and 45 into the sleeve 38 for driving longitudinal and rotational movement of the tip 36.

The drive motor comprises a housing 50 formed by an upper half 51 and a lower half 52 both of semi-cylindrical shape with the two portions engaged together to surround the drive elements with the fiber extending axially along a center of the housing. At the front 53 of the housing is provided a boss defining a bore 54 within which the sleeve 38 forms a sliding fit. This acts to guide the movement of the sleeve at the forward end of the housing.

Within the housing is provided a first annular mount 55 and a second annular mount 56 spaced rearwardly from the first. Between the first annular mount and the front boss is provided a first encoder 57 and behind the second annular mount 56 is provided a second encoder 58.

The first annular mount 55 mounts a first rotatable drive disk 59 on bearings 60. The second annular mount carries a second drive disk 61 on bearings 62. Each of the drive disks is of the same shape including a generally flat disk portion with a cylindrical portion 63 on the rear of the disk and lying on a common axis with the disk portion. The bearings are mounted between a cylindrical inner face of the annular portion 55, 56 and an outside surface of the cylindrical portions 63. Each of the disks is therefore mounted for rotation about the axis of the fiber along the axis of the housing.

The disk 59 includes a central plug portion 64 which closes the center hole of the disk portion and projects into the cylindrical portion 63. The plug portion has a chamfered or frusto-conical lead in section 65 converging to a drive surface 66 surrounding the drive member 44 and having a common cross sectional shape therewith. Thus the tip portion 41 of the sleeve 38 can slide along the axis of the housing and engage into the conical lead in section 65 so as to pass through the drive surface or bore 66 until the drive member 44 engages into the surface 66. In the position, rotation of the disk 59 drives rotation of the sleeve 38 and therefore of the fiber. As the drive portion 44 has a constant cross section, it can slide through the drive surface 66 forwardly and rearwardly.

The disk 61 includes a plug member 67 which engages into the central opening in the disk member 61. The plug 67 has an inner surface 68 which defines a female screw thread for co-operating with a lead screw 69. The lead screw 69 has an inner bore 70 surrounding the sleeve 38 so that the sleeve 38 is free to rotate and move relative to the bore 70. The lead screw 69 also passes through the cylindrical portion 63 of the disk 61. However rotation of the disk 61 acts to drive the lead screw longitudinally of the axis of the housing and therefore of the axis of the sleeve 38. A rear end 71 of the lead screw is attached to a clamping member 72. The clamping member 72 includes a first fixed portion 73 attached to the rear end 71 of the lead screw and a second loose portion 74 which can be clamped into engaging the fixed portion so as to clamp the end stop members 45 in position within the clamping member. The loose portion 74 is clamped in place by screws 75. The top segment 45A of the end stop 45 engages into a receptacle 76 in the fixed portion 73 so as to orient the sleeve 38 relative to the lead screw.

The disks 59 and 61 are driven in a ratchetting action by drive motors 77 and 78 respectively. In the preferred embodiment the drive motors are provided by piezo-electric drive elements in which a piezo-electric crystal is caused to oscillate thus actuating a reciprocating action which is used to drive by a ratchet process angular rotation of the respective disk.

The reciprocating action of the piezo-electric crystal 77 and 78 is provided by two such motors 77 co-operating with the disk 59 and two motors 78 co-operating with the disk 61. Each motor is carried on a mounting bracket 77A, 78A which is suitably attached to the housing.

The end clamp 72 is generally rectangular in cross section and slides within a correspondingly rectangular cross section duct 72A within the housing. Thus the lead screw 69 is held against rotation and is driven axially by the rotation of the disk 61 while the fiber is free to rotate relative to the lead screw.

In other alternative arrangements (not shown), the ratchetting action can be effected by a longitudinally moveable cable driven from the device controller 25 outside the room 11. In a further alternative arrangement, the motor may comprise a hydraulic or pneumatic motor which again effects a ratchetting action by reciprocating movement of a pneumatically or hydraulically driven prime mover.

Thus selected rotation of a respective one of the disks can be effected by supplying suitable motive power to the respective motor.

The respective encoder 57, 58 detects the instantaneous position of the disk and particularly the sleeve portion 63 of the disk which projects into the interior of the encoder. The sleeve portion therefore carries a suitable elements which allows the encoder to detect accurately the angular orientation of the respective disk. In this way the position of the disks can be controlled by the device controller 25 accurately moving the disk 59 to control the angular orientation of the fiber and accurately moving the disk 61 to control the longitudinal position of the fiber. The longitudinal position is of course obtained by moving the lead screw longitudinally which carries the end stop 45 longitudinally. The movements are independent so that the fiber can be rotated while held longitudinally stationary.

As the motor driving movement of the fiber is used while the magnet and the MRI system is in operation, it is essential that the motor and the associated control elements that are located within the room 11 are compatible with the MRI system. For this purpose, the power supply or control cable 24 and the motor must both be free from ferromagnetic components which would be responsive to the magnetic field. In addition it is necessary that the motor 22 and the cable 24 are both properly shielded against interference with the small radio frequency signals which must be detected for the MRI analysis to be effective.

Figure 7:
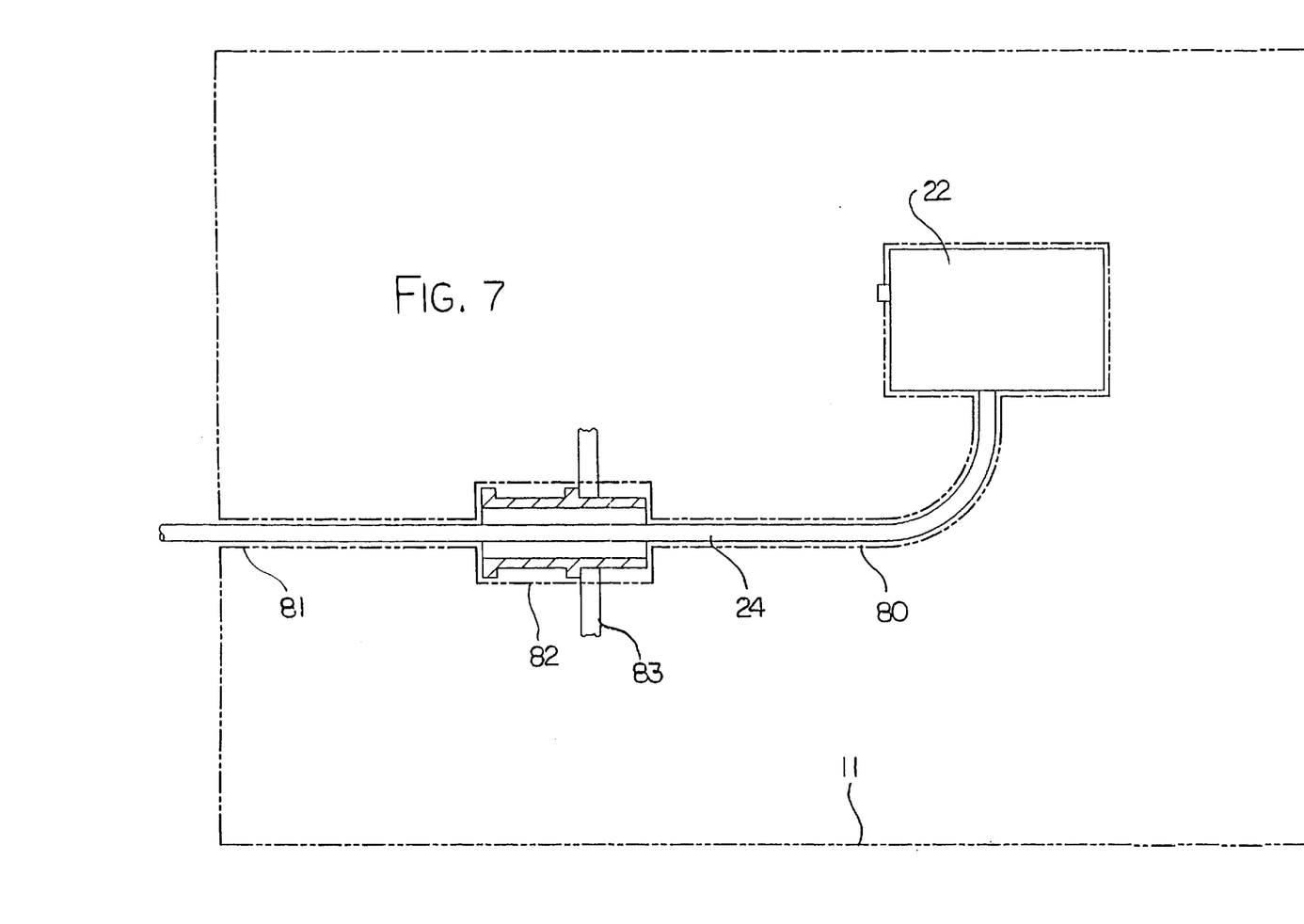
FIG. 7 is a schematic illustration of the shielding of the apparatus of FIG. 1.

As shown in FIG. 7, therefore, the room 11 is surrounded by a conductor which prevents penetration of radio frequency interference into the area within the room at the magnet. In addition the cable 24 and the motor 22 are surrounded by a conductor 80 which extends through an opening 81 in the conductor at the wall 11 through a cable port 82 within the wall 83 of the enclosure so that the whole of the motor and the cable are encased within the conductor 80 which is connected to the conductor within the wall. Thus the conductor 80 acts as a "worm hole" in the shielding thus retaining the motor 22 and the cable 24 effectively external to the shielding at the periphery of the room. The use of a Piezo-electric crystal to drive disks is particularly suitable and provides particular compatibility with the MRI system but other drive systems can also be used as set forth previously.

Figure 8:
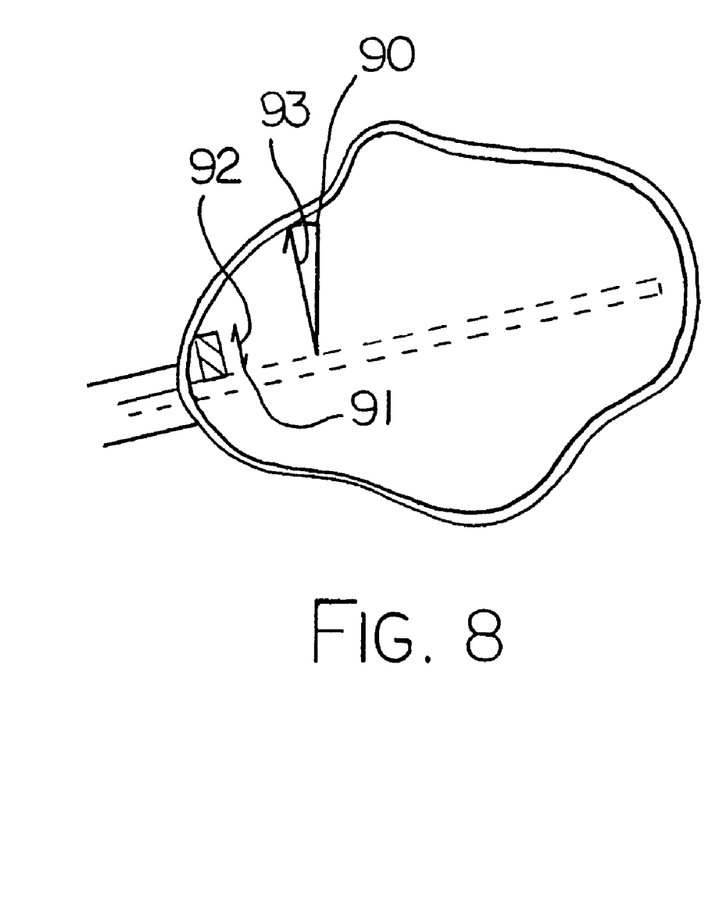
FIG. 8 is a schematic illustration of the effect of the apparatus on a tumour or other mass to be ablated.

In the method of operation, the patient is located on the patient table and so to be restrained so that the head of the patient is held fixed within the magnet to prevent motion artefacts. The MRI system is then operated in conventional manner to generate an image of the portion, generally a tumour, to be excised. The surgeon alone or in conjunction with suitable software available to one skilled in the art then analyses the images developed to locate the closed area surrounding the volume of the tumour and defining the external perimeter of the tumour as indicated at FIG. 8 at 90. The surgeon also determines the best route for directing the cannula to the tumour to avoid damaging intervening tissue and to provide a best course to the centre of the tumour which may be irregular in shape.

Having determined the course and direction of the cannula, the opening 34 is formed and the cannula inserted as previously described.

With the cannula in place, the motor is mounted on the frame and the frame adjusted to locate the motor so that the fiber can be inserted directly along the length of the cannula. With the motor properly aligned along the axis of the cannula, the fiber is inserted through the bore of the motor and into the cannula so as to extend through the cannula until the tip emerges just out of the outer end of the cannula. The distance of the motor from the cannula can be adjusted so that the tip just reaches the end of the cannula when the lead screw is fully retracted and the end stop is located in place in the clamp 72.

With the motor and fiber thus assembled, the MRI system is arranged to carry out experiments which generate temperature measurements in the boundary zone 90. The temperature is detected over the full surface area of the boundary rather than simply at a number of discrete locations. While the experiments to detect the temperature are continued, the fiber is moved longitudinally to commence operation at a first position just inside the volume of the tumour. At a selected angular orientation of the beam, pulses of radiation are emitted by the laser and transmitted into the tumour through the beam 37. The pulses are continued while the temperature in the boundary layer 90 is detected. As the pulses supply heat energy into the volume of the tumour, the tumour is heated locally basically in the volume defined by the beam but also heat is conducted out of the volume of the beam into the remainder of the tumour at a rate dependent upon the characteristics of the tumour itself. Heating at a localised area defined by the beam is therefore continued until the heat at the boundary layer 90 is raised to the predetermined coagulation temperature of the order of 55 to 65° C. Once the boundary layer reaches this temperature, heating at that zone is discontinued and the fiber is moved either longitudinally or angularly or both to move to the next zone of the tumour to be heated. It is not necessary to predict the required number of pulses in advance since the detection of temperature at the boundary is done in real time and sufficiently quickly to prevent overshoot. However, predictions can be made in some circumstances in order to carry out the application of the heat energy as quickly as possible.

It is of course desirable to effect heating as quickly as possible so as to minimize the operation duration. For this purpose the number of pulses per second may also be varied based upon the above predication depending upon the characteristics of the tumour as detected in the initial analysis. However the energy application rate cannot be so high that the temperature rises too quickly so that over shooting of the desired temperature at the boundary occurs with the possibility of damage to tissue outside the boundary. The rate of energy application is therefore selected depending upon the size and consistency of the tumour to effect heating at a controlled rate in order to achieve the required temperature at the boundary without the possibility of over shoot. The rate of heat application can also be varied in dependence upon the distance of the boundary from the axis of the fiber. Thus the axis of the fiber is indicated at 91 in FIG. 8 and a first distance 92 of the beam to the boundary is relatively short at the entry point of the fiber into the tumour and increases to a second larger distance 93 toward the center of the tumour.

In some cases it is desirable to maintain the fiber stationary at a first selected longitudinal position and at a first selected angular orientation until the temperature at the boundary reaches the required temperature. In this case the fiber is then rotated through an angle approximately equal to the beam angle to commence heating at a second angular orientation with the fiber being rotated to a next angular orientation only when heating at that second orientation is complete. In this way heating is effected at each position and then the fiber rotated to a next orientation position until all angular orientations are completed.

After a first disk shaped portion of the tumour is thus heated, the fiber is moved longitudinally through a distance dependant upon the diameter of the tumour at that location and dependant upon the beam angle so as to ensure the next disk shaped volume of tumour heated contains all of the tumour structure without intervening localised portions of the tumour which are not heated to the required temperature. Thus the fiber is moved longitudinally in steps which may vary in distance depending upon the diameter and structure of the tumour as determined by the initial analysis. However the total heating of the tumour is preferably determined by the temperature at the boundary without the necessity for analysis of the temperatures of the tumour inside the boundary or any calculations of temperature gradients within the tumour.

When the complete boundary of the tumour has been heated to the predetermined coagulation temperature, the surgery is complete and the apparatus is disassembled for removal of the fiber and the cannula from the patient.

The system allows direct and accurate control of the heating by controlling the temperature at the surface area defined by the boundary of the tumour so that the whole of the volume of the tumour is properly heated to the required temperature without the danger of heating areas external to the tumour beyond the coagulation temperature.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

What is claimed is:

1. An apparatus comprising:
    a magnetic resonance imaging system arranged to generate an image from a sample and including a magnet to generate a magnetic field and an antenna for detecting radio frequency signals from the sample;
    a member located within and arranged to be moved within the magnetic field;
    and a motor having a drive coupling thereto for driving movement of the member, the motor including an element for generating a motive force for the motor;
    the motor including no ferro-magnetic components such that it is usable in the magnetic field;
    and the motor and the drive coupling being shielded by a surrounding conductor to prevent interference with the radio frequency signals.

2. The apparatus according to claim 1 wherein the drive element comprises a piezo-electric motor.

3. An apparatus for laser treatment on a part of a patient comprising:
    an optical fiber having an inlet end and an outlet end;
    a laser source for supplying light energy into the fiber at the inlet end;
    a light deflector at the outlet end for directing the light in a beam at an angle to a longitudinal axis of the fiber at the outlet end such that a first rotation of the fiber about the axis causes the beam to rotate about the axis;
    a rigid elongate cannula arranged for insertion into the part of the patient;

the cannula having a bore arranged for receiving a portion of the fiber adjacent the outlet end extending therethrough such that the end can pass through the cannula into engagement with the part of the patient;

a drive assembly for causing a first longitudinal movement of the fiber relative to the cannula along its length and for causing a second rotational movement of the fiber about its axis the fiber having a reinforcing sleeve member surrounding and attached to a portion of the fiber adjacent the outlet end, the sleeve member holding the fiber against lateral bending during said longitudinal movement and against torsional twisting during said rotational movement.

4. The apparatus according to claim 3 wherein the sleeve includes a first portion at the outlet end which is formed of a first material which is substantially rigid to support that portion of the fiber projecting beyond the end of the cannula and a second portion connected to and extending from the first portion to the drive assembly, the second portion being formed of a second material which is stiff but less rigid than the first portion to allow some flexing when the fiber is inserted into the cannula.

5. The apparatus according to claim 3 wherein the reinforcing sleeve includes an engagement portion attached thereto for engaging the drive assembly including a portion of polygonal cross-section for engaging into a drive collar of corresponding cross-section of the drive assembly for driving rotational movement of the fiber and including a shoulder section for engaging against a drive member of the drive assembly for driving longitudinal movement of the fiber.

6. A method for effecting treatment in a patient comprising:

identifying a volume in the patient the whole of which volume is to be heated to a required temperature, the volume being defined by a peripheral surface of the volume;

providing a heat source and applying heat to the volume within the patient by;

providing the heat source on an invasive probe having a longitudinal axis;

inserting the probe into the volume;

arranging the probe to cause directing of heat in a direction at an angle to the longitudinal axis such that a heating effect of the probe lies in a disk surrounding the axis;

and arranging the direction of the heat so as to define a heating zone which forms a limited angular orientation of heating within the disk such that, as the probe is rotated, the probe causes heating of different angularly separate zones of the volume within the disk;

operating a non-invasive detection system to generate a series of output signals over a period of time representative of temperature in the patient as the temperature of the patient changes during that time;

using the output signals to monitor the temperature at the peripheral surface of the volume as the temperature changes over the period of time;

with the probe at a fixed axial position, rotating the probe about the axis so that the heating zone lies at a first angular position to define a first heating zone;

using a measure of the temperature at that part of the peripheral surface of the volume in the first zone as the determining factor as to when to halt heating by the probe to the first zone;

subsequently rotating the probe about the axis so that the heating zone lies in at a second angular position to define a second heating zone;

and using a measure of the temperature at that part of the peripheral surface of the volume in the second zone as the determining factor as to when to halt heating by the probe to the second zone.

7. The method according to claim 6 including subsequently moving the probe axially within the volume so as to move the disk of the heating effect axially within the volume from a first disk position to second disk position.

8. The method according to claim 6 including varying the power applied by the heat source during the heating of each heating zone.

9. The method according to claim 6 wherein the heat source comprises a laser and an optical fiber extending along the probe for communicating light from the laser, with a light directing element at an end of the fiber for directing the light from the laser to a predetermined direction relative to the fiber.

10. The method according to claim 9 wherein the fiber has a reinforcing sleeve member surrounding and attached to a portion of the fiber adjacent the outlet end, the sleeve member being driven to effect longitudinal movement and rotational movement of the fiber and holding the fiber against lateral bending during said longitudinal movement and against torsional twisting during said rotational movement.

11. The apparatus according to claim 10 wherein the non-invasive detection system comprises a magnetic resonance imaging system including a magnet to generate a magnetic field for the imaging system and an antenna for detecting radio frequency signals from the patient; and wherein the drive assembly includes a motor for driving movement of the probe, the motor including substantially no ferro-magnetic components such that it is usable in the magnetic field and the motor and a drive coupling thereto being shielded by a surrounding conductor to prevent interference with the radio frequency signals.

12. The apparatus according to claim 10 wherein the drive assembly comprises a piezo-electric motor.

13. The apparatus according to claim 10 including means for varying the power applied by the heat source during the heating of each heating zone.

14. An apparatus for effecting treatment of a patient comprising:

a heat source arranged to apply heat to the volume within the patient including;
an invasive probe having a longitudinal axis;
the probe being arranged to cause directing of heat in a direction at an angle to the longitudinal axis such that a heating effect of the probe lies in a disk surrounding the axis;
the probe being arranged such that the direction of the heat defines a heating zone which forms a limited angular orientation of heating within the disk such that, as the probe is rotated, the probe causes heating of different angularly separate zones of the volume within the disk;

a drive assembly for driving movement of the probe;

a non-invasive detection system arranged:
to provide entry and storage of a definition of a peripheral surface of the volume within the patient;
to generate a series of output signals over a period of time representative of temperature in the patient at the peripheral surface of the volume as the temperature changes during that time;

and a probe control system arranged, with the probe at a fixed axial position:
to rotate the probe about the axis so that the heating zone lies at a first angular position to define a first heating zone;

to use a measure of the temperature at that part of the peripheral surface of the volume in the first zone as the determining factor as to when to halt-heating by the probe to the first zone;

subsequently to rotate the probe about the axis so that the heating zone lies in at a second angular position to define a second heating zone;

and to use a measure of the temperature at that part of the peripheral surface of the volume in the second zone as the determining factor as to when to halt heating by the probe to the second zone.

15. The apparatus according to claim 14 wherein the probe is movable by the drive assembly axially within the volume so as to move the disk of the heating effect axially within the volume from a first disk position to second disk position.

16. The apparatus according to claim 15 wherein the sleeve includes a first portion at the outlet end which is formed of a first material which is substantially rigid and a second portion connected to and extending from the first portion to the drive assembly, the second portion being formed of a second material which is stiff but less rigid than the first portion to allow some flexing.

17. The apparatus according to claim 15 wherein the reinforcing sleeve includes an engagement portion attached thereto for engaging the drive assembly including a portion of polygonal cross-section for engaging into a drive collar of corresponding cross-section of the drive assembly for driving rotational movement of the fiber and including a shoulder section for engaging against a drive member of the drive assembly for driving longitudinal movement of the fiber.

18. The apparatus according to claim 15 wherein the drive assembly includes a driven member rotatable about an axis and a reciprocating drive element and wherein the driven member includes a sleeve arranged to receive the fiber therethrough, the fiber and sleeve being shaped such that rotation of the driven member causes rotation of the fiber about the axis while allowing longitudinal movement of the fiber relative to the sleeve.

19. The apparatus according to claim 18 wherein the driven member comprises a first disk and there is provided a second driven disk parallel to the first disk, the second disk having a female threaded bore therein and wherein the fiber has attached thereto a screw engaging the bore such that rotation of the second driven disk about the axis causes the screw to effect movement of the fiber longitudinally along the axis and rotation of the first disk causes rotation of the fiber about the axis.

20. The apparatus according to claim 15 wherein the drive assembly includes a driven member rotatable about an axis and a reciprocating drive element, wherein the driven member has a female threaded bore therein and wherein the fiber has attached thereto a screw engaging the bore such that rotation of the driven member about the axis causes the screw to effect movement of the fiber longitudinally along the axis.

21. The apparatus according to claim 14 wherein the heat source comprises a laser and an optical fiber for communicating light from the laser with a light directing element at an end of the fiber for directing the light from the laser to a predetermined direction relative to the fiber.

22. The apparatus according to claim 21 wherein the fiber has a reinforcing sleeve member surrounding and attached to a portion of the fiber adjacent the outlet end, the sleeve member being driven to effect longitudinal movement and rotational movement of the fiber and holding the fiber against lateral bending during said longitudinal movement and against torsional twisting during said rotational movement.

23. An apparatus for effecting treatment of a patient comprising:

a heat source arranged to apply heat to the volume within the patient including;

a drive assembly for driving movement of the heat source;

a magnetic resonance imaging system arranged to generate an image from the patient and including a magnet to generate a magnetic field and an antenna for detecting radio frequency signals from the patient;

the drive assembly including a motor having a drive coupling thereto for driving movement of the member;

the motor including substantially no ferro-magnetic components such that it is usable in the magnetic field;

and the motor and the drive coupling being shielded by a surrounding conductor to prevent interference with the radio frequency signals.

24. The apparatus according to claim 23 wherein the heat source comprises:

an invasive probe having a longitudinal axis;

the probe being arranged to cause directing of heat in a direction at an angle to the longitudinal axis such that a heating effect of the probe lies in a disk surrounding the axis;

the probe being arranged such that the direction of the heat defines a heating zone which forms a limited angular orientation of heating within the disk;

the probe being rotatable by the drive assembly about the axis so that the heating zone, as the probe is rotated, causes heating of different angular segments within the disk;

and the probe being movable by the drive assembly axially within the volume so as to move the disk of the heating effect axially within the volume from a first disk position to second disk position.

25. The apparatus according to claim 24 wherein the heat source comprises a laser, an optical fiber for communicating light from the laser, a mounting for the optical fiber allowing invasive insertion of an end of the fiber forming the probe into the volume and a light directing element at an end of the fiber for directing the light from the laser to a predetermined direction relative to the fiber.

26. The apparatus according to claim 25 wherein the fiber has a reinforcing sleeve member surrounding and attached to a portion of the fiber adjacent the outlet end, the sleeve member being driven to effect longitudinal movement and rotational movement of the fiber and holding the fiber against lateral bending during said longitudinal movement and against torsional twisting during said rotational movement.

27. The apparatus according to claim 26 wherein the drive assembly includes a first driven member rotatable about an axis and a reciprocating drive element for driving the driven member and wherein the driven member includes a tube arranged to receive the sleeve member therethrough, the sleeve member and tube being shaped such that rotation of the driven member causes rotation of the sleeve member and the tube about the axis while allowing longitudinal movement of the sleeve member relative to the tube.

28. The apparatus according to claim 27 wherein the drive assembly includes a second driven member which has a female threaded bore therein and wherein the fiber and sleeve member has attached thereto a screw engaging the bore such that rotation of the second driven member about the axis causes the screw to effect movement of the sleeve member longitudinally along the axis.

29. The apparatus according to claim 28 wherein the first driven member comprises a first disk and the second driven member comprises a second disk parallel to the first disk.

30. The apparatus according to claim 29 wherein the first and second driven members are each driven by a piezoelectric motor.

31. An apparatus for effecting treatment of a patient comprising:

an optical fiber having an inlet end and an outlet end;

a laser source for supplying light energy into the fiber at the inlet end;

a light deflector at the outlet end for directing the light in a beam at an angle to a longitudinal axis of the fiber at the outlet end such that a first rotation of the fiber about the axis causes the beam to rotate about the axis;

a drive assembly spaced from the end of the fiber for causing a first longitudinal movement of the fiber along its length and for causing a second rotational movement of the fiber about its axis;

the fiber having a stiff reinforcing sleeve member surrounding and attached to a portion of the fiber adjacent the outlet end, the sleeve member engaging the drive assembly so as to receive said longitudinal movement and rotational movement therefrom and holding the fiber against lateral bending during said longitudinal movement and against torsional twisting during said rotational movement to communicate said movement from the drive assembly to the end of the fiber.

32. The apparatus according to claim 31 wherein the reinforcing sleeve member includes an engagement portion attached thereto for engaging the drive assembly including a portion of polygonal cross-section for engaging into a drive collar of corresponding cross-section of the drive assembly for driving rotational movement of the fiber and including a shoulder section for engaging against a drive member of the drive assembly for driving longitudinal movement of the fiber.

33. The apparatus according to claim 31 wherein the drive assembly includes a first driven member rotatable about an axis and a reciprocating drive element for driving the driven member and wherein the driven member includes a tube arranged to receive the sleeve member therethrough, the sleeve member and tube being shaped such that rotation of the driven member causes rotation of the sleeve member about the axis while allowing longitudinal movement of the sleeve member relative to the tube.

34. The apparatus according to claim 33 wherein the drive assembly includes a second driven member which has a female threaded bore therein and wherein the fiber and sleeve member has attached thereto a screw engaging the bore such that rotation of the second driven member about the axis causes the screw to effect movement of the sleeve member longitudinally along the axis.

35. The apparatus according to claim 34 wherein the first driven member comprises a first disk and the second driven member comprises a second disk parallel to the first disk.

36. The apparatus according to claim 34 wherein the first and second driven members are each driven by a piezoelectric motor.

* * * * *